US006858617B2

(12) United States Patent
Adams

(10) Patent No.: US 6,858,617 B2
(45) Date of Patent: Feb. 22, 2005

(54) SUBSTITUTED IMIDAZOLE COMPOUNDS

(75) Inventor: Jerry L. Adams, Wayne, PA (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 10/359,436

(22) Filed: Jun. 2, 2003

(65) Prior Publication Data
US 2004/0002509 A1 Jan. 1, 2004

Related U.S. Application Data

(63) Continuation of application No. 09/700,826, filed as application No. PCT/US99/11455 on May 25, 1999, now abandoned.
(60) Provisional application No. 60/086,645, filed on May 26, 1998.

(51) Int. Cl.$^7$ .................... A61K 31/506; C07D 403/04
(52) U.S. Cl. ..................... 514/275; 544/330; 544/331; 544/332
(58) Field of Search ............................... 544/330, 331, 544/332; 514/275

(56) References Cited

U.S. PATENT DOCUMENTS

| | | | |
|---|---|---|---|
| 2,833,779 A | 5/1958 | Fields | 260/296 |
| 3,707,475 A | 12/1972 | Lombardino | 260/309 |
| 3,772,441 A | 11/1973 | Lombardino | 424/273 |
| 3,929,807 A | 12/1975 | Fitzi | 260/294.8 R |
| 3,940,486 A | 2/1976 | Fitzi | 424/263 |
| 4,058,614 A | 11/1977 | Baldwin | 424/263 |
| 4,199,592 A | 4/1980 | Cherkofsky | 424/273 |
| 4,447,431 A | 5/1984 | Sallmann | 424/246 |
| 4,503,065 A | 3/1985 | Wilkerson | 514/396 |
| 4,565,875 A | 1/1986 | Cavender | 548/336 |
| 4,686,231 A | 8/1987 | Bender et al. | 514/333 |
| 4,822,805 A | 4/1989 | Tasasugi et al. | 514/341 |
| 4,886,807 A | 12/1989 | Kitamura et al. | 514/254 |
| 5,545,669 A | 8/1996 | Adams et al. | 514/562 |
| 5,559,137 A | 9/1996 | Adams et al. | 514/341 |
| 5,593,991 A | 1/1997 | Adams et al. | 514/235.2 |
| 5,593,992 A | 1/1997 | Adams et al. | 514/235.8 |
| 5,656,644 A | 8/1997 | Adams et al. | 514/341 |
| 5,658,903 A | 8/1997 | Adams et al. | 514/235.8 |
| 5,663,334 A | 9/1997 | Sheldrake et al. | 544/123 |
| 5,670,527 A | 9/1997 | Adams et al. | 514/341 |
| 5,686,455 A | 11/1997 | Adams et al. | 514/256 |
| 5,716,955 A | 2/1998 | Adams et al. | 514/235.8 |
| 5,716,972 A | 2/1998 | Adams et al. | 514/314 |
| 5,739,143 A | 4/1998 | Adams et al. | 514/275 |
| 5,756,499 A | 5/1998 | Adams et al. | 514/235.8 |
| 5,777,097 A | 7/1998 | Lee et al. | 536/24.31 |
| 5,783,664 A | 7/1998 | Lee et al. | 530/350 |
| 5,811,549 A | 9/1998 | Adams et al. | 544/123 |
| 5,864,036 A | 1/1999 | Adams et al. | 544/123 |
| 5,869,043 A | 2/1999 | McDonnell et al. | 424/94.1 |
| 5,869,660 A | 2/1999 | Adams et al. | 544/122 |
| 5,871,934 A | 2/1999 | Lee et al. | 435/7.1 |
| 5,916,891 A | 6/1999 | Adams et al. | 514/256 |
| 5,917,043 A | 6/1999 | Sisko | 544/332 |
| 5,929,076 A | 7/1999 | Adams et al. | 514/252 |
| 5,955,366 A | 9/1999 | Lee et al. | 435/471 |
| 5,969,184 A | 10/1999 | Adams et al. | 564/154 |
| 5,977,103 A | 11/1999 | Adams et al. | 514/235.25 |
| 5,998,425 A | 12/1999 | Adams et al. | 514/275 |
| 6,008,235 A | 12/1999 | Adams et al. | 514/333 |
| 6,096,739 A | 8/2000 | Feuerstein | 514/235.2 |
| 6,150,373 A | 11/2000 | Harris et al. | 514/258 |
| 6,235,760 B1 | 5/2001 | Feuerstein | 514/341 |
| 6,288,062 B1 | 9/2001 | Adams et al. | 514/236.8 |
| 6,335,340 B1 | 1/2002 | Gallagher et al. | 514/252.05 |
| 6,362,193 B1 | 3/2002 | Adams et al. | 514/274 |

FOREIGN PATENT DOCUMENTS

| | | |
|---|---|---|
| EP | 0 477 049 A1 | 8/1991 |
| EP | 0 477 049 B1 | 8/1991 |
| GB | 2 123 830 | 2/1984 |
| WO | WO 91/19497 | 12/1991 |
| WO | WO 92/10190 | 6/1992 |
| WO | WO 92/10498 | 6/1992 |
| WO | WO 92/12154 | 7/1992 |
| WO | WO 93/14081 | 7/1993 |
| WO | WO 93/14082 | 7/1993 |
| WO | WO 94/19350 | 9/1994 |
| WO | WP 95/02591 | 1/1995 |
| WO | WO 95/03297 | 2/1995 |
| WO | WO 95/09847 | 4/1995 |
| WO | WO 95/09851 | 4/1995 |
| WO | WO 95/09852 | 4/1995 |
| WO | WO 95/09853 | 4/1995 |
| WO | WO 95/13067 | 5/1995 |
| WO | WO 95/31451 | 11/1995 |
| WO | WO 95/33461 | 12/1995 |
| WO | WO 96/21452 | 7/1996 |
| WO | WO 96/21654 | 7/1996 |
| WO | WO 96/40143 | 12/1996 |
| WO | WO 97/05877 | 2/1997 |
| WO | WO 97/05878 | 2/1997 |
| WO | WO 97/12876 | 4/1997 |

(List continued on next page.)

OTHER PUBLICATIONS

Wang et al., "Structural Basis of Inhibitor Selectivity in MAP Kinases", Structure, 1998 vol. 6 No. 9, pp. 117–128.

Jackson, J.R. et al., "Pharmacological Effects of SB 220025, A Selective Inhibitor of P38 Mitogen–Activated Protein Kinase, in Angiogenesis and Chronic Inflammatory Disease Models", Journal of Pharmacology and Experimental Therapeutics, vol. 284, No. 2, 1998, pp. 687–692.

(List continued on next page.)

Primary Examiner—Richard L. Raymond
(74) Attorney, Agent, or Firm—Dara L. Dinner; Stephen Venetianer; Charles M. Kinzig

(57) ABSTRACT

Novel 1,4,5-substituted imidazole compounds and compositions for use in therapy as ERK/MAP inhibitors of ERK/MAP mediated diseases.

10 Claims, 2 Drawing Sheets

FOREIGN PATENT DOCUMENTS

Figure 1:
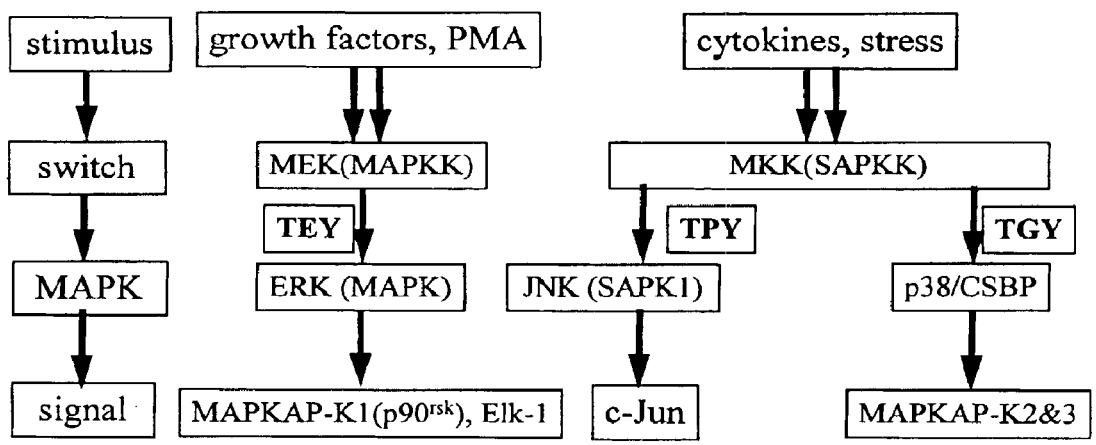

| | | |
|---|---|---|
| WO | WO 97/16426 | 5/1997 |
| WO | WO 97/16441 | 5/1997 |
| WO | WO 97/16442 | 5/1997 |
| WO | WO 97/23479 | 7/1997 |
| WO | WO 97/25045 | 7/1997 |
| WO | WO 97/25046 | 7/1997 |
| WO | WO 97/25047 | 7/1997 |
| WO | WO 97/25048 | 7/1997 |
| WO | WO 97/32583 | 9/1997 |
| WO | WO 97/33883 | 9/1997 |
| WO | WO 97/35855 | 10/1997 |
| WO | WO 97/35856 | 10/1997 |
| WO | WO 97/36587 | 10/1997 |
| WO | WO 97/47618 | 12/1997 |
| WO | WO 98/03484 | 1/1998 |
| WO | WO 98/06715 | 2/1998 |
| WO | WO 98/07425 | 2/1998 |
| WO | WO 98/16230 | 4/1998 |
| WO | WO 98/22109 | 5/1998 |
| WO | WO 98/22457 | 5/1998 |
| WO | WO 98/24780 | 6/1998 |
| WO | WO 98/25619 | 6/1998 |
| WO | WO 98/27098 | 6/1998 |
| WO | WO 98/28292 | 7/1998 |
| WO | WO 98/47892 | 10/1998 |
| WO | WO 98/48799 | 11/1998 |
| WO | WO 98/52558 | 11/1998 |
| WO | WO 98/52937 | 11/1998 |
| WO | WO 98/52940 | 11/1998 |
| WO | WO 98/52941 | 11/1998 |
| WO | WO 98/56377 | 12/1998 |
| WO | WO 98/56788 | 12/1998 |
| WO | WO 98/57966 | 12/1998 |
| WO | WO 99/00357 | 1/1999 |
| WO | WO 99/01130 | 1/1999 |
| WO | WO 99/01131 | 1/1999 |
| WO | WO 99/01136 | 1/1999 |
| WO | WO 99/01449 | 1/1999 |
| WO | WO 99/01452 | 1/1999 |
| WO | WO 99/03837 | 1/1999 |
| WO | WO 99/17776 | 4/1999 |
| WO | WO 99/18942 | 4/1999 |
| WO | WO 99/32110 | 7/1999 |
| WO | WO 99/32121 | 7/1999 |
| WO | WO 99/42592 | 8/1999 |
| WO | WO 99/57101 | 11/1999 |
| WO | WO 99/57253 | 11/1999 |
| WO | WO 99/58128 | 11/1999 |
| WO | WO 99/58502 | 11/1999 |
| WO | WO 99/58523 | 11/1999 |
| WO | WO 99/59959 | 11/1999 |
| WO | WO 99/59960 | 11/1999 |
| WO | WO 99/61426 | 12/1999 |
| WO | WO 99/61437 | 12/1999 |
| WO | WO 99/61440 | 12/1999 |
| WO | WO 99/64400 | 12/1999 |
| WO | WO 01/01688 | 1/2000 |
| WO | WO 00/07980 | 2/2000 |
| WO | WO 00/07991 | 2/2000 |
| WO | WO 00/10563 | 2/2000 |
| WO | WO 00/06563 | 3/2000 |
| WO | WO 00/12074 | 3/2000 |
| WO | WO 00/12497 | 3/2000 |
| WO | WO 00/17175 | 3/2000 |
| WO | WO 00/18738 | 4/2000 |
| WO | WO 00/19824 | 4/2000 |
| WO | WO 00/20402 | 4/2000 |
| WO | WO 00/23072 | 4/2000 |
| WO | WO 00/25791 | 5/2000 |
| WO | WO 00/26209 | 5/2000 |
| WO | WO 00/31063 | 6/2000 |
| WO | WO 00/31065 | 6/2000 |
| WO | WO 00/31072 | 6/2000 |
| WO | WO 00/35911 | 6/2000 |
| WO | WO 00/39116 | 7/2000 |
| WO | WO 00/40243 | 7/2000 |
| WO | WO 00/41698 | 7/2000 |
| WO | WO 00/43384 | 7/2000 |
| WO | WO 00/59541 | 10/2000 |
| WO | WO 00/75131 | 12/2000 |
| WO | WO 01/00229 | 1/2001 |
| WO | WO 01/19322 | 3/2001 |
| WO | WO 01/37837 | 5/2001 |
| WO | WO 01/38313 | 5/2001 |
| WO | WO 01/64679 | 9/2001 |
| WO | WO 02/07772 | 1/2002 |
| WO | WO 02/058695 | 8/2002 |
| WO | WO 02/059083 | 8/2002 |
| WO | WO02/060869 | 8/2002 |

OTHER PUBLICATIONS

Armarego, W. J. Chem. Soc., (JCSOA9) p. 561 (1962).
Badger et al., "Protective Effect of SK&F 86002, a Novel Dual Inhibitor of Arachidonic Acid ...", Circulatory Shock, vol. 27, 1991, pp. 51–61.
Becker et al., J. Immunol., 147, p. 4307 (1991).
Boehm et al., J. Med. Chem. 39, pp. 3929–3937 (1996).
Bradlerova et al., Chem. Zvesti, 29 (6), pp. 795–802 (1975).
Colotta et al., J. Immunol., 132(2), p. 936 (1984).
de Silva et al., J. Chem. Soc., 4, pp. 685–690, (1995).
Dinarello et al., Rev.Infect.Disease, 6, p. 51 (1984).
Dinarello, J.Clin.Immun., 5(5), p. 287–297 (1985).
Engel & Steglich, Liebigs Ann. Chem., 1916 (1978).
Ferles et al., Collect. Czech. Chem. Commun., 5 (46), pp. 1167–1172 (1981).
Fischer et al., Rec.Trav.Chim.Pays.Bas., 84, p. 439 (1965).
Fulmer et al., J. Heterocycl. Chem., 17 (4), pp. 799–800 (1980).
Gallahger et al., Bioorganic & Medicinal Chem. vol. 5, No. 1, pp. 49–64 (1997).
Garigipati, R., Tetrahedron Letters, 31, p. 190 (1989).
Gilbert, Synthesis, pp. 30–32 (1972).
Griswold et al., "Differentiation in vivo of classical non–steroidal antiinflammatory drugs ... ", Drugs Exptl. Clin. Res., XIX(6), 1993, pp. 243–248.
Griswold et al., "Effect of Inhibots of Eicosanoid Metabolism in Murine Collagen–Induced Arthritis", Arthritis and Rheumatism, vol. 31, No. 11, Nov. 1998, pp. 1406–1412.
Ishibashi, Chem. Pharm. Bull., 37(8), pp. 2214–2216 (1989).
Johnson, P.A., J.Chem.Soc., Perkin Trans., vol. 1, pp. 895–905 (1996).
Jurkowski–Kowalczyk, Rocz. Chem., 51 (6), pp. 1191–9 (1977).
Katritzky, Synthesis, pp. 45–47 (1993).
Kawasaki et al., J. Bio. Chem., 272(30), pp. 18518–18521.
Kumada et al., Tetrahedron Letters, 22, p. 5319 (1981).
Lamartina et al., Boll. Chim. Farm., 129 (12), pp. 314–316 (1990).
Lee et al., "Bicyclic Imidazoles as a Novel Class of Cytokine Biosynthesis Inhibitors", Annals NY Academy of Sciences, vol. 696, 1993, pp. 149–170.
Mikailu et al., Zh. Obshch. Khim., 56(7), pp. 1513–1517 (1986).
Morton et al., Tetrahedron Letters, 4123 (1982).

Olivera et al., "Beneficial Effects of SK&F 105809, a Novel Cytokine–Suppressive Agent, in Murine Models of Endotoxin Shock", Circulatory Shock, 37, 1992, pp. 301–306.
Poli et al., Proc. Nat'l Acad.Sci., 87, p. 782–784 (1990).
Pridgen, J.Org.Chem., 47, p. 4319 (1982).
Protecting Groups in Organic Synthesis, Second Edition, Greene TW and Wuts PGM, Wiley–Interscience, New York 1991, pp. 10–174 (hydroxyl and phenolic) and pp. 309–403 (NH protection).
R.P.Soni, Aust.J.Chem., 35, p. 1493–6 (1982).
Santilli et al., "Thieno[2,3–d]pyrimidines. I. A New Method for the Preparation of Esters . . . ", J. Heterocycl Chem., vol. 8, 1971, pp. 445–453.
Simon et al., J. Immunol. Methods, 84, p. 85 (1985).
Snieckus, V., Tetrahedron Letters, 29, 2135 (1988).
Stille, J.Amer.Chem.Soc., 109, p. 5478 (1978).
Strzybny et al., J. Org. Chem., 28, p. 3381 (1963).
Szucs et al., Chem. Zvesti, 26 (4), pp. 354–359 (1972).
Szucs et al., Acta fac. Pharm. Univ. Commenianae, 30, pp. 127–46 (1977).
Terashimia, M., Chem.Pharm.Bull., 11, p. 4755 (1985).
Thompson, W.J., et al., J.Org.Chem., 49, p. 5237 (1984).
Uno, Bull. Chem. Soc. Japan., vol. 69, pp. 1763–1767 (1996).
VanLeusen et al., J.O.C., 42, p. 1153 (1977).
Vartanyan et al., 40, (9), pp. 552–560 (1987).
Votta et al., "Inhibition of Human Monocyte IL–1 Production by SK&F 86002", Int. J. Immunotherapy, VI(1), 1990, pp. 1–12.
Warrior et al., "Development of a p38 Kinase Binding Assay for Hight Throughtput Screening", Journal of Biomolecular Screening, vol. 4 No. 3, 1999, pp. 129–135.
Wilson et al., Chemistry & Biology, vol. 4, No. 6, pp. 423–431 (1997).
Zavyalov, et al., Khim Farm Zh, 26(3), p. 88 (1992) (With Translation).

US 6,858,617 B2

SUBSTITUTED IMIDAZOLE COMPOUNDS

This application is a continuation of U.S. Ser. No. 09/700,826, filed 21 Nov. 2000 (abandoned), which is the §371 national stage of PCT/US99/11455, filed 25 May 1999, which claims the benefit of priority from provisional application U.S. Ser. No. 60/086,645, filed 26 May 1998.

This invention relates to a novel group of imidazole compounds, processes for the preparation thereof, the use thereof in treating ERK/MAP mediated diseases and pharmaceutical compositions for use in such therapy.

There remains a need for treatment, in this field, for compounds which are capable of inhibiting the actions ERK/MAP kinase.

SUMMARY OF THE INVENTION

This invention relates to the novel compounds of Formula (I) and pharmaceutical compositions comprising a compound of Formula (I) and a pharmaceutically acceptable diluent or carrier.

This invention relates to a method of treating a ERK/MAP kinase mediated disease, in a mammal in need thereof, which comprises administering to said mammal an effective amount of a compound of Formula (I).

This invention also relates to a method of inhibiting the ERK/MAP kinase in a mammal in need thereof, which comprises administering to said mammal an effective amount of a compound of Formula (I).

Accordingly, the present invention provides a compound of Formula (I):

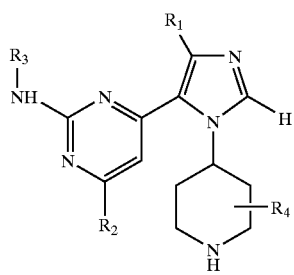

(I)

$R_1$ is hydrogen, $C_{1-5}$ alkyl, halogen, $C_{1-5}$ alkoxy, or aryl$C_{1-5}$ alkyl;
$R_2$ is hydrogen, $C_{1-5}$ alkyl, aryl, aryl$C_{1-5}$ alkyl, heteroaryl, heteroaryl$C_{1-5}$ alkyl, heterocyclic, heterocyclic $C_{1-5}$ alkyl;
$R_3$ is hydrogen, or $C_{1-3}$ alkyl;
$R_4$ is hydrogen, $C_{1-5}$ alkyl, aryl, aryl$C_{1-5}$ alkyl, heteroaryl, heteroaryl$C_{1-5}$ alkyl, heterocyclic, heterocyclic $C_{1-5}$ alkyl;
or a pharmaceutically acceptable salt thereof.

DETAILED DESCRIPTION OF THE INVENTION

In Formula (I), suitable $R_1$ moieties include hydrogen, $C_{1-5}$ alkyl, halogen, $C_{1-5}$ alkoxy or aryl$C_{1-5}$ alkyl. Preferably the moiety is a $C_{1-5}$ alkyl, which may be branched or unbranched.

Suitably, $R_2$ is hydrogen, $C_{1-5}$ alkyl, aryl, aryl$C_{1-5}$ alkyl, heteroaryl, heteroaryl$C_{1-5}$ alkyl, heterocyclic, heterocyclic $C_{1-5}$ alkyl, wherein all of these moieties may be optionally substituted as defined below.

When $R_2$ is a heterocyclic or heterocyclic alkyl moiety, the heterocyclic ring is a saturated or partially unsaturated 4–10 membered ring system in which one or more rings contain one or more heteroatoms selected from the group consisting of N, O, or S; such as, but not limited to pyrrolindinyl, piperidine, morpholino, tetra-hydropyran, tetrahydrothiopyranyl, tetrahydrothipyransulfinyl, tetrahydro-thiopyransulfonyl, pyrrolindinyl, or an indole ring.

When $R_2$ is a heteroaryl or heteroarylalkyl moiety, the heteroaryl portion is a 5–10 membered aromatic ring system in which one or more rings contain one or more heteroatoms selected from the group consisting of N, O or S, such as, but not limited to pyrrole, pyrazole, furan, thiophene, quinoline, isoquinoline, quinazolinyl, pyridine, pyrimidine, oxazole, thiazole, thiadiazole, tetrazole, triazole, imidazole, or benzimidazole.

Suitably, $R_3$ is hydrogen, or $C_{1-3}$ alkyl (branched or unbranched).

Suitably, $R_4$ is hydrogen, $C_{1-5}$ alkyl, aryl, aryl$C_{1-5}$ alkyl, heteroaryl, heteroaryl$C_{1-5}$ alkyl, heterocyclic, heterocyclic $C_{1-5}$ alkyl, and wherein all of these moieties may be optionally substituted as defined below. Suitable heteroaryl and heterocyclic containing moieties for use herein are the same as those described above for $R_2$.

As used herein, "optionally substituted" unless specifically defined shall mean such groups as halogen, such as fluorine, chlorine, bromine or iodine; hydroxy; hydroxy substituted $C_{1-10}$alkyl; $C_{1-10}$ alkoxy, such as methoxy or ethoxy; halosubstituted $C_{1-10}$ alkoxy; S(O)m alkyl, wherein m is 0, 1 or 2, such as methyl thio, nethylsulfinyl or methyl sulfonyl; amino, mono & di-$C_{1-5}$ alkyl substituted amino, such as the moiety $R_7R_{17}$ wherein $R_7$ and $R_{17}$ are hydrogen or $C_{1-5}$ alkyl, or where the $R_7$ and $R_{17}$ substituent groups may together with the nitrogen to which they are attached cyclize to form a 5 to 7 membered ring which optionally includes an additional heteroatom selected from O/N/S; $C_{1-10}$ alkyl, $C_{3-7}$ cycloalkyl, or $C_{3-7}$ cycloalkyl $C_{1-10}$ alkyl group, such as methyl, ethyl, propyl, isopropyl, t-butyl, etc. or cyclopropyl methyl; halosubstituted $C_{1-10}$ alkyl, such CF$_2$CF$_2$H, or CF$_3$; an optionally substituted aryl, such as phenyl, or an optionally substituted arylalkyl, such as benzyl or phenethyl, wherein these aryl moieties may also be substituted one to two times by halogen; hydroxy; hydroxy substituted alkyl; $C_{1-10}$ alkoxy; S(O)$_m$alkyl; amino, mono & di-substituted amino, such as in the NR$_7$R$_{17}$ group; alkyl, or CF$_3$.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of Formula (I) may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

The following terms, as used herein, refer to:
"halo" or "halogens", include the halogens: chloro, fluoro, bromo and iodo.
"$C_{1-5}$alkyl" or "alkyl"—includes both straight and branched chain radicals of 1 to 5 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

The term "cycloalkyl" is used herein to mean cyclic radicals, preferably of 3 to 8 carbons, including but not limited to cyclopropyl, cyclopentyl, cyclohexyl, and the like.

"aryl"—phenyl and naphthyl;

"heteroaryl" (on its own or in any combination, such as "heteroaryloxy", or "heteroaryl alkyl")—a 5–10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, thiazole, thiadiazole, tetrazole, triazole, imidazole, or benzimidazole.

"heterocyclic" (on its own or in any combination, such as "heterocyclylalkyl")—a saturated or partially unsaturated 4–10 membered ring system in which one or more rings contain one or more heteroatoms selected from the group consisting of N, O, or S; such as, but not limited to, pyrrolidine, piperidine, piperazine, morpholine, tetrahydropyran, or imidazolidine.

The term "aralkyl" or "heteroarylalkyl" or "heterocyclicalkyl" is used herein to mean $C_{1-4}$ alkyl as defined above attached to an aryl, heteroaryl or heterocyclic moiety as also defined herein unless otherwise indicate.

It is recognized that the compounds of the present invention may exist as stereoisomers, regioisomers, or diastereiomers. These compounds may contain one or more asymmetric carbon atoms and may exist in racemic and optically active forms. All of these compounds are included within the scope of the present invention.

Exemplified compounds of Formula (I) include: 1-(4-Piperidinyl)-4-methyl-5-(3-amino-pyrimidin-4-yl) imidazole; or a pharmaceutically acceptable salt thereof.

The compounds of Formula (I) may be obtained by applying synthetic procedures, some of which are illustrated in the Schemes herein. The synthesis provided for in these Schemes is applicable for the producing compounds of Formula (I) having a variety of different $R_1$, $R_2$, $R_3$, and $R_4$ groups which are reacted, employing optional substituents which are suitably protected, to achieve compatibility with the reactions outlined herein. Subsequent deprotection, in those cases, then affords compounds of the nature generally disclosed.

Suitable protecting groups for use with the imidazole nitrogen are well known in the art and described in many references, for instance, Protecting Groups in Organic Synthesis, Greene T W, Wiley-Interscience, New York, 1981. Preferably an example of an imidazole nitrogen protecting group is tetrahydropyranyl.

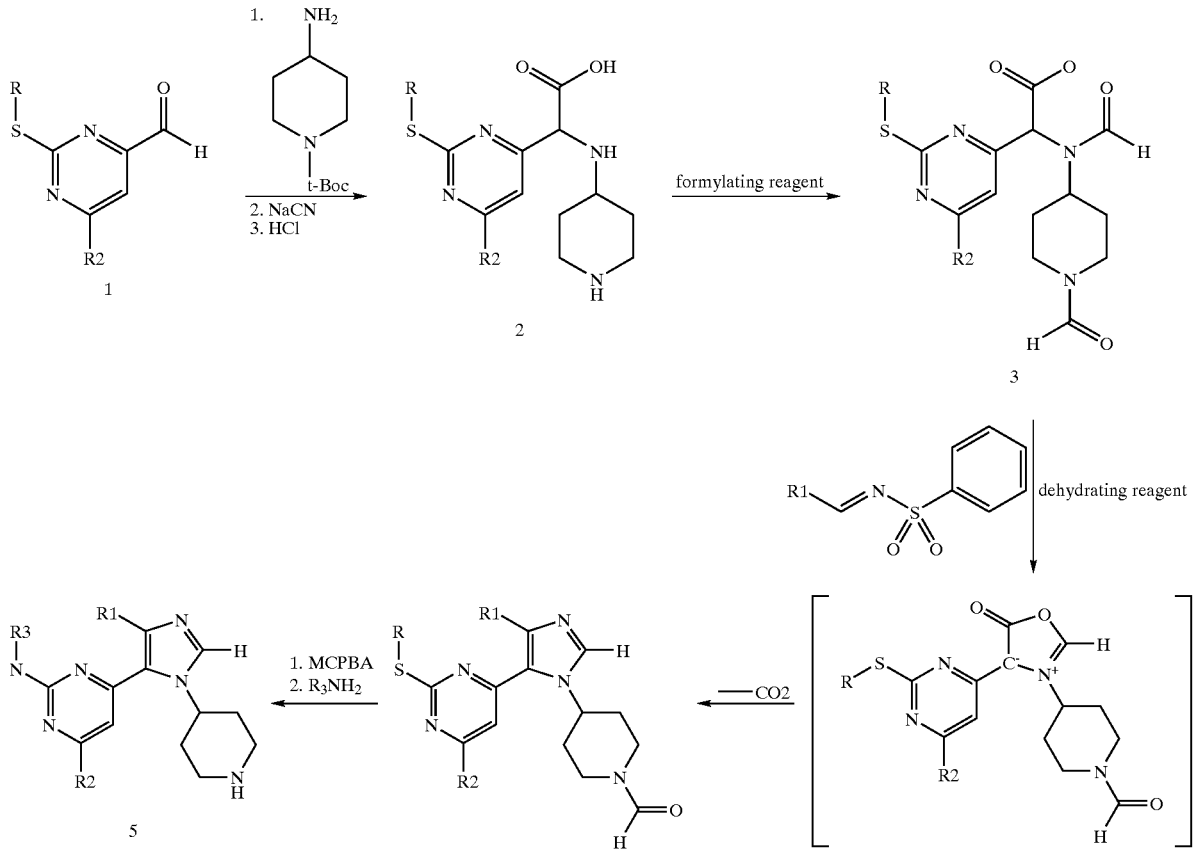

SCHEME 1

The synthesis of 4-formyl-2-thioalkylpyrimidine (R=Pr, R2=H), 1, is described in U.S. Pat. No. 5,658,903, whose disclosure is incorporated herein by reference in its entirety. Formation of the imine of 1 with t-Boc-4-aminopiperidine under dehydrating conditions, for example $MgSO_4$ in $CH_2Cl_2$, followed by addition of cyanide affords the α-aminonitrile. Hydrolysis of the nitrile under acidic conditions yields the deprotected free amino acid, 2. Formylation using the mixed anhydride of formic and acetic acids, or some other suitable formulating agent, provides the required precursor, 3, for the 1,3-dipolar cycloaddition. Isolation of 3 may not be required as under the dehydrating conditions described for the formylation of 2, cyclodehydration to form the intermediate munchnone may occur. Reaction of the thus formed munchnone with a sulfonylimine (formed by condensation of the sulfonamide with $R_2COH$) provides the imidazole cycloaddition adduct, 4. The general procedures for this chemistry and the specific application for the formation of imidazoles are described in Consonni, R. et. al. *J.Chem. Research* (S) p188 (1991) and Croce, P. D., et. al. *J. Heterocyclic Chem.* 24, 1793 (1987). Oxidation of the 2-thioalkylpyrimidine to the more activated sulfoxide and/or sulfone leaving group allows facile displacement of the sulfur with a variety of nucleophiles, including ammonia and simple alkyl amines ($R_3$), to afford the desired 2-aminopyrimidines, 5.

Pharmaceutically acid addition salts of compounds of Formula (I) may be obtained in known manner, for example by treatment thereof with an appropriate amount of acid in the presence of a suitable solvent.

Methods of Treatment

The compounds of Formula (I) or a pharmaceutically acceptable salt thereof can be used in the manufacture of a medicament for the prophylactic or therapeutic treatment of an ERK kinase mediated disease state in a human, or other mammal, which is exacerbated or caused by excessive or unregulated ERK2/MAP kinase activation by such mammal's cell, such as but not limited to monocytes and/or macrophages.

Intracellular signal transduction is the means by which cells respond to extracellular stimuli. Regardless of the nature of the cell surface receptor (e. g. protein tyrosine kinase or seven-transmembrane G-protein coupled), protein kinases and phosphatases along with phopholipases are the essential machinery by which the signal is further transmitted within the cell [Marshall, J. C. *Cell*, 80, 179–278 (1995)]. Protein kinases can be categorized into five classes with the two major classes being, tyrosine kinases and serine/threonine kinases depending upon whether the enzyme phosphorylates its substrate(s) on specific tyrosine (s) or serine/theronine (s) residues [Hunter, T. *Methods in Enzymology* (*Protein Kinase Classification*) p. 3, Hunter, T.; Sefton, B. M.; eds. vol. 200, Academic Press; San Diego, 1991].

The MAP kinase or ERK (extracellular signal regulated kinase) family is a novel set of kinases which are intimately involved with and in many cases required for the intracellular transmission of mitogenic or growth signals. ERK1 and ERK2 were the first two members of the family to be identified. A characteristic requirement for activation of these kinases is the dual phosphorylation on the TEY sequence of the kinase activation loop, a reaction which is effected by a select group of upstream kinases, know as MAP kinase kinases (MAPKK). Additional signal transduction components both upstream and downstream of ERK1/ERK2 have been identified and pathway(s) leading from activation of an extracellular receptor to transcriptional regulation have been elucidated. [Marshall, C. J. *Cell*, 80, 179 (1995); Herskowitz, I. *Cell*, 80, 187 (1995); Hunter, T. *Cell*, 80, 225 (1995); Seger, R., and Krebs, E. G. *FASEB J.*, 726–735 (1995)]. A general outline of this sequence for the ERK kinases and related MAP kinases is shown in FIG. 1. The ERK2 kinase may also be referred to as p44MAP kinase.

The JNK and p38 kinases constitute two additional arms of the MAP kinase pathway which are primarily activated by "stress" signals. All three pathways are independent and are composed of additional family members. Although independent there is considerable crosstalk between the pathways and in most cases an extracellular signal will activate several parts of the pathway; hence is the unique pattern and strength of the signals which emerge from these kinase cascades which will influence the cellular response. The different MAP family members are distinguished by the identify of the dual activation sequence. The JNK kinases contain TPY and the p38 kinases TGY, whereas as noted earlier the ERK kinases contain TEY.

Figure 2:
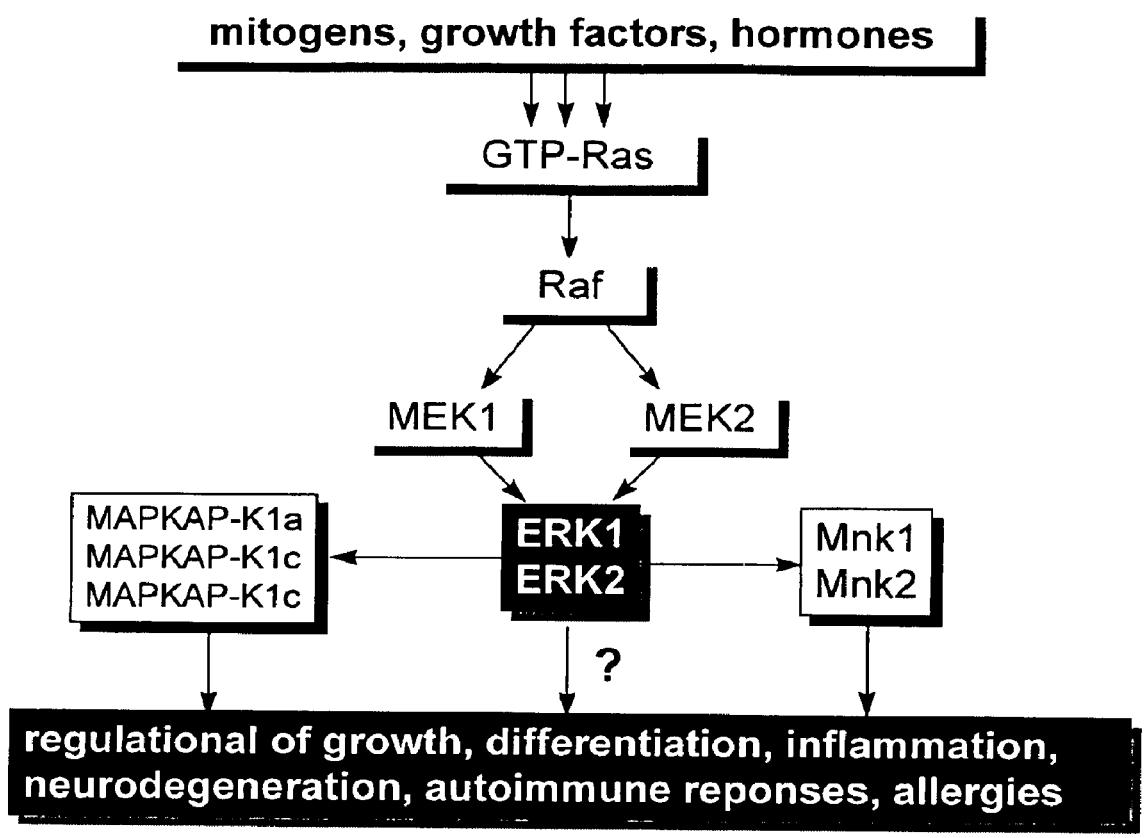

Growth or mitogenic signals are the most important activators of the ERK kinases and considerable evidence supports the requirement of ERK signaling for response to these stimuli (FIG. 2 illustrates a more detailed description of the ERK1/ERK2 cascade). Hence inhibition of the ERK kinase has potential for therapeutic utility in a number of disease states, most importantly to block the uncontrolled growth of cancer cells. Other potential utilities of ERK kinase inhibitors are inflammation, allergy, autoimmune disease and neurodegeneration (FIG. 2).

The compounds of Formula (I) may also be used topically in the treatment or prophylaxis of topical disease states mediated by or exacerbated by excessive ERK/MAP kinase production, such as inflamed joints, eczema, psoriasis and other inflammatory skin conditions such as sunburn; inflammatory eye conditions including conjunctivitis; pyresis, pain and other conditions associated with inflammation.

The compounds of Formula (I) are administered in an amount sufficient to inhibit ERK/MAP activity such that it is regulated down to normal levels, or in some case to sub-normal levels, so as to ameliorate or prevent the disease state.

The discovery that the compounds of Formula (I) are inhibitors of ERK/MAP may be based upon the effects of the compounds of Formulas (I) on in vitro assays which are described herein.

As used herein, the term "inhibiting the activity ERK/MAP kinase refers to:

a) a decrease of excessive in vivo levels of the kinase in a human to normal or sub-normal levels by inhibition of the in vivo release of the kinase by all cells, including but not limited to monocytes or macrophages;

b) a down regulation, at the genomic level, of excessive in vivo levels of the kinase in a human to normal or sub-normal levels;

c) a down regulation, by inhibition of the direct synthesis of the kinase as a postranslational event; or d) a down regulation, at the translational level, of excessive in vivo levels of the kinase in a human to normal or sub-normal levels.

In order to use a compound of Formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the Formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of Formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of Formula (I), the daily oral dosage regimen will preferably be from about 0.1 to about 80 mg/kg of total body weight, preferably from about 0.2 to 30 mg/kg, more preferably from about 0.5 mg to 15 mg. The daily parenteral dosage regimen about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The novel compounds of Formula (I) may also be used in association with the veterinary treatment of mammals, other than humans, in need of inhibition of ERK/MAP kinase inhibition or production.

The invention will now be described by reference to the following biological examples which are merely illustrative and are not to be construed as a limitation of the scope of the present invention.

BIOLOGICAL EXAMPLES

The ERK/MAP inhibiting effects of compounds of the present invention are determined by the following in vitro assay:

The ERK kinase assay was performed using a commercially available kit (P44$^{MPK}$, Upstate Biotechnology Inc.) Kinase activity was determined by measuring the incorporation of $^{32}$P from γ-[$^{32}$P]ATP into an EGFR-derived peptide (T669) having the following sequence: KREL VEPLTPS-GEAPNQALLR. Reactions (30 μl) contained 25 mM Hepes buffer, pH 7.4, 8 mM MgCl$_2$; 10 μM Na-vanadate; 1 mM EDTA, 0.8 μCi/170 μM $^{32}$P/ATP; 0.4 ng ERK kinase; and 0.4 mM peptide. Compounds were incubated for 20 min at 4° C. with enzyme and peptide prior to adding ATP. Reactions were incubated for 10 min at 30° C. and were stopped by adding 10 μL of 0.3 M phosphoric acid. Phosphorylated peptide was isolated from the reaction mixture on phosphocellulose filter paper (p81). Filters were washed with 75 mM phosphoric acid and counted using a liquid scintillation counter.

SYNTHETIC EXAMPLES

The invention will now be described by reference to the following examples which are merely illustrative and are not to be construed as a limitation of the scope of the present invention. All temperatures are given in degrees centigrade, all solvents are highest available purity and all reactions run under anhydrous conditions in an argon atmosphere unless otherwise indicated.

In the Examples, all temperatures are in degrees Centigrade (° C.). Mass spectra were performed upon a VG Zab mass spectrometer using fast atom bombardment or on a micromass platform electrospray ionization mass spectrometer in the positive ion mode using 95:5 CH$_3$CN/CH$_3$OH with 1% formic acid as the carrier solvent, unless otherwise indicated. $^1$H-NMR (hereinafter "NMR") spectra were recorded at 250 MHz using a Bruker AM 250 or Am 400 spectrometer. Multiplicities indicated are: s=singlet, d=doublet, t=triplet, q=quartet, m=multiplet and br indicates a broad signal. Sat. indicates a saturated solution, eq indicates the proportion of a molar equivalent of reagent relative to the principal reactant. Flash chromatography is run over Merck Silica gel 60 (230–400 mesh).

Example 1

1-(4-Piperidinyl)-4-methyl-5-(3-amino-pyrimidin-4-yl)imidazole

The title compound can be prepared by the synthetic route illustrated in Scheme 2 using the reaction conditions described in Consonni, R. et. al. *J.Chem. Research* (S) p188 (1991) and Croce, P. D., et. al. *J. Heterocyclic Chem.* 24, 1793 (1987) or modifications thereof which are apparent to one skilled in the art of organic synthesis. The synthesis of the requisite starting pyrimidine aldehyde and the t-Boc-4-aminopiperidine are described in U.S. Pat. No. 5,670,527 whose disclosure is incorporated herein by reference in its entirety.

SCHEME 2

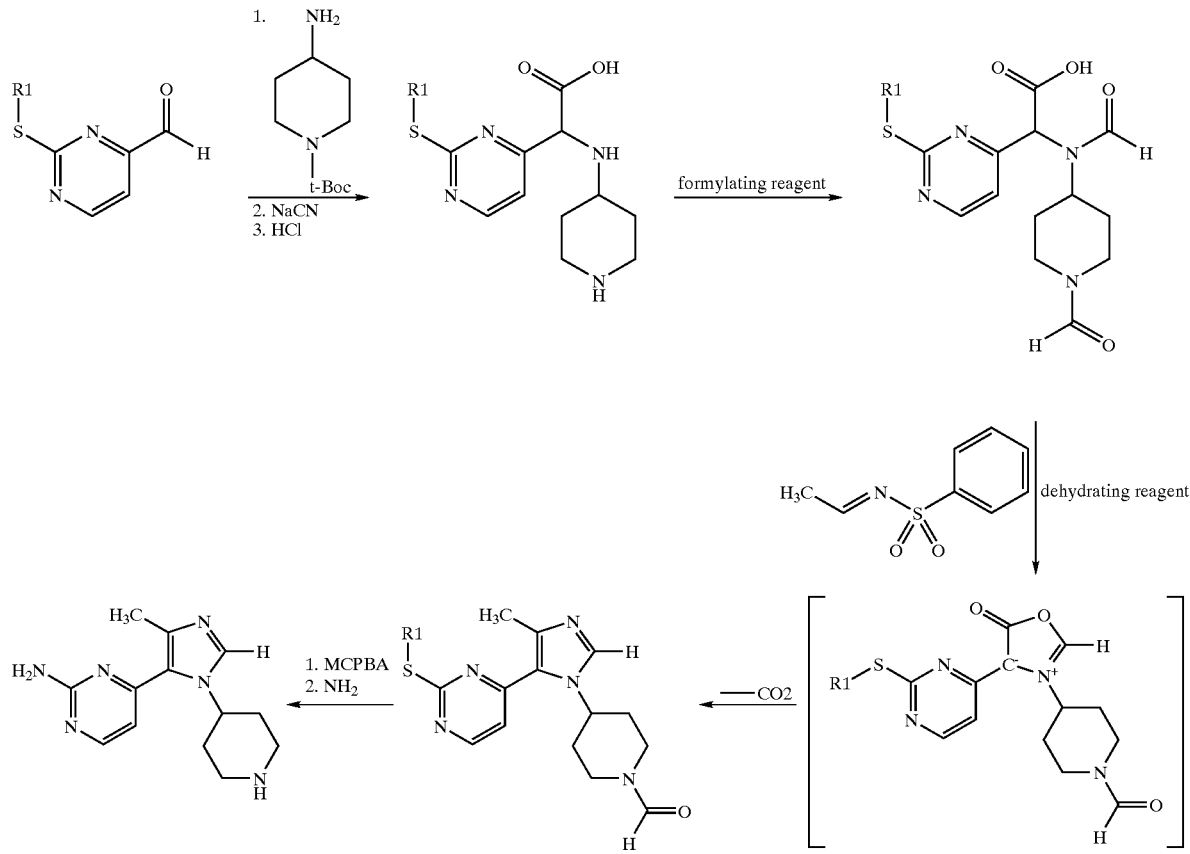

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. A compound represented by the formula:

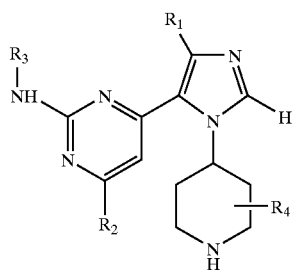

(I)

wherein $R_1$ is hydrogen, halogen, $C_{1-5}$ alkyl, $C_{1-5}$ alkoxy, or aryl$C_{1-5}$ alkyl;

$R_2$ is hydrogen, $C_{1-5}$ alkyl, aryl, aryl$C_{1-5}$ alkyl, pyrrole, pyrazole, furan, thiophene, quinoline, isoquinoline, quinazolinyl, pyridine, pyrimidine, oxazole, thiazole, thiadiazole, tetrazole, triazole, imidazole, benzimidazole, pyrrole $C_{1-5}$ alkyl, pyrazole $C_{1-5}$ alkyl, furan $C_{1-5}$ alkyl, thiophene $C_{1-5}$ alkyl, quinoline $C_{1-5}$ alkyl, isoquinoline $C_{1-5}$ alkyl, quinazolinyl $C_{1-5}$ alkyl, pyridine $C_{1-5}$ alkyl, pyrimidine $C_{1-5}$ alkyl, oxazole $C_{1-5}$ alkyl, thiazole $C_{1-5}$ alkyl, thiadiazole $C_{1-5}$ alkyl, tetrazole $C_{1-5}$ alkyl, triazole $C_{1-5}$ alkyl, imidazole $C_{1-5}$ alkyl, benzimidazole $C_{1-5}$ alkyl, pyrrolindinyl, piperidine, morpholino, tetra-hydropyran, tetrahydrothiopyranyl, tetrahydrothiopyransulfinyl, tetrahydro-thiopyransulfonyl, pyrrolindinyl, indole, pyrrolindinyl $C_{1-5}$ alkyl, piperidine $C_{1-5}$ alkyl, morpholino $C_{1-5}$ alkyl, tetra-hydropyran $C_{1-5}$ alkyl, tetrahydrothiopyranyl $C_{1-5}$ alkyl, tetrahydrothiopyransulfinyl $C_{1-5}$ alkyl, tetrahydro-thiopyransulfonyl $C_{1-5}$ alkyl, pyrrolindinyl $C_{1-5}$ alkyl, or indole $C_{1-5}$ alkyl, and wherein all of these moieties may be optionally substituted by halogen; hydroxy; hydroxy substituted $C_{1-10}$alkyl; $C_{1-10}$ alkoxy; halosubstituted $C_{1-10}$ alkoxy; S(O)m alkyl, wherein m is 0, 1 or 2; amino, mono & di-$C_{1-5}$ alkyl substituted amino; $C_{1-10}$ alkyl; $C_{3-7}$ cycloalkyl; $C_{3-7}$cycloalkyl $C_{1-10}$ alkyl; halosubstituted $C_{1-10}$ alkyl; an optionally substituted aryl, or an optionally substituted arylalkyl, wherein these aryl moieties are also optionally substituted one to two times by halogen; hydroxy; hydroxy substituted alkyl; $C_{1-10}$ alkoxy; S(O)$_m$alkyl; amino, mono & di-substituted amino, alkyl, or $CF_3$;

$R_3$ is hydrogen, or $C_{1-3}$ alkyl;

$R_4$ is hydrogen, $C_{1-5}$ alkyl, aryl, aryl$C_{1-5}$ alkyl, pyrrole, pyrazole, furan, thiophene, quinoline, isoquinoline, quinazolinyl, pyridine, pyrimidine, oxazole, thiazole, thiadiazole, tetrazole, triazole, imidazole, benzimidazole, pyrrole $C_{1-5}$ alkyl, pyrazole $C_{1-5}$ alkyl, furan $C_{1-5}$ alkyl, thiophene $C_{1-5}$ alkyl, quinoline $C_{1-5}$ alkyl, isoquinoline $C_{1-5}$ alkyl, quinazolinyl $C_{1-5}$ alkyl, pyridine $C_{1-5}$ alkyl, pyrimidine $C_{1-5}$ alkyl, oxazole $C_{1-5}$ alkyl, thiazole $C_{1-5}$ alkyl, thiadiazole $C_{1-5}$ alkyl, tetrazole $C_{1-5}$ alkyl, triazole $C_{1-5}$ alkyl, imidazole $C_{1-5}$ alkyl, benzimidazole $C_{1-5}$ alkyl, pyrrolindinyl, piperidine, morpholino, tetra-hydropyran, tetrahydrothiopyranyl, tetrahydrothiopyransulfinyl, tetrahydro-thiopyransulfonyl, pyrrolindinyl, indole, pyrrolindinyl $C_{1-5}$ alkyl, piperidine $C_{1-5}$ alkyl, morpholino $C_{1-5}$ alkyl, tetra-hydropyran $C_{1-5}$ alkyl, tetrahydrothiopyranyl $C_{1-5}$ alkyl, tetrahydrothiopyransulfinyl $C_{1-5}$ alkyl, *tetrahydro-thiopyransulfonyl $C_{1-5}$ alkyl, pyrrolindinyl $C_{1-5}$ alkyl, or indole $C_{1-5}$ alkyl, and wherein all of these moieties may be optionally substituted by halogen; hydroxy; hydroxy substituted $C_{1-10}$alkyl; $C_{1-10}$ alkoxy; halosubstituted $C_{1-10}$ alkoxy; S(O)m alkyl, wherein m is 0, 1 or 2; amino, mono & di-$C_{1-5}$ alkyl substituted amino; $C_{1-10}$ alkyl; $C_{3-7}$ cycloalkyl; $C_{3-7}$cycloalkyl $C_{1-10}$ alkyl; halosubstituted $C_{1-10}$ alkyl; an optionally substituted aryl, or an optionally substituted arylalkyl, wherein these aryl moieties are also optionally substituted one to two times by halogen; hydroxy; hydroxy substituted alkyl; $C_{1-10}$ alkoxy; S(O)$_m$alkyl; amino, mono & di-substituted amino, alkyl, or $CF_3$;

or a pharmaceutically acceptable salt thereof.

2. The compound according to claim 1 wherein $R_1$ is a $C_{1-5}$ alkyl.

3. The compound according to claim 2 wherein $R_2$ is hydrogen or pyrrolindinyl, piperidine, morpholino, tetra-hydropyran, tetrahydrothiopyranyl, tetrahydrothiopyransulfinyl, tetrahydro-thiopyransulfonyl, pyrrolindinyl, indole, pyrrolindinyl $C_{1-5}$ alkyl, piperidine $C_{1-5}$ alkyl, morpholino $C_{1-5}$ alkyl, tetra-hydropyran $C_{1-5}$ alkyl, tetrahydrothiopyranyl $C_{1-5}$ alkyl, tetrahydrothiopyransulfinyl $C_{1-5}$ alkyl, tetrahydro-thiopyransulfonyl $C_{1-5}$ alkyl, pyrrolindinyl $C_{1-5}$ alkyl, or indole $C_{1-5}$ alkyl.

4. The compound according to claim 2 wherein $R_3$ is hydrogen.

5. The compound according to claim 2 wherein $R_4$ is hydrogen.

6. A pharmaceutical composition comprising an effective amount of a compound according to claim 1 and a pharmaceutically acceptable carrier or diluent.

7. A method of treating inflammation in a mammal in need thereof, which comprises administering to said mammal an effective amount of a compound of Formula (I) according to claim 1.

8. A method of treating an allergic response in a mammal in need thereof, which comprises administering to said mammal an effective amount of a compound of Formula (I) according to claim 1.

9. A method of treating an autoimmune response in a mammal in need thereof, which comprises administering to said mammal an effective amount of a compound of Formula (I) according to claim 1.

10. A method of treating a neurogenerative disease in a mammal in need thereof, which comprises administering to said mammal an effective amount of a compound of Formula (I) according to claim 1.

* * * * *